United States Patent
Kalgren et al.

(10) Patent No.: US 10,639,488 B2
(45) Date of Patent: May 5, 2020

(54) TAP SENSOR-ENABLED IMD

(71) Applicant: Cardiac Pacemakers, Inc., St. Paul, MN (US)

(72) Inventors: James R. Kalgren, Lino Lakes, MN (US); Keith R. Maile, New Brighton, MN (US); Jonathan H. Kelly, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 301 days.

(21) Appl. No.: 15/050,461

(22) Filed: Feb. 22, 2016

(65) Prior Publication Data

US 2016/0243373 A1 Aug. 25, 2016

Related U.S. Application Data

(60) Provisional application No. 62/119,796, filed on Feb. 23, 2015.

(51) Int. Cl.
| | |
|---|---|
| *A61N 1/39* | (2006.01) |
| *A61B 5/11* | (2006.01) |
| *A61B 5/00* | (2006.01) |
| *A61N 1/372* | (2006.01) |
| *A61B 5/01* | (2006.01) |
| *A61B 5/021* | (2006.01) |
| *A61B 5/026* | (2006.01) |

(Continued)

(52) U.S. Cl.
CPC .......... *A61N 1/3987* (2013.01); *A61B 5/0015* (2013.01); *A61B 5/7475* (2013.01); *A61N 1/37217* (2013.01); *A61N 1/3962* (2013.01); *A61B 5/0031* (2013.01); *A61B 5/026* (2013.01); *A61B 5/0432* (2013.01); *A61B 5/1117* (2013.01)

(58) Field of Classification Search
CPC ............ A61N 1/37211; A61N 1/37264; A61N 1/37282; A61N 1/08; G06F 19/3412; A61B 5/0006; A61B 5/0031; A61B 5/0432
USPC ...................................................... 607/59–60
See application file for complete search history.

(56) References Cited

U.S. PATENT DOCUMENTS

| | | |
|---|---|---|
| 5,304,206 A | 4/1994 | Baker et al. |
| 5,312,446 A | 5/1994 | Holschbach et al. |
| 5,891,044 A | 4/1999 | Golosarsky et al. |

(Continued)

FOREIGN PATENT DOCUMENTS

WO      WO9743003 A1     11/1997

OTHER PUBLICATIONS

International Search Report and Written Opinion issued in PCT/US2016/018990 dated Aug. 22, 2016, 15 pages.

(Continued)

*Primary Examiner* — Jon Eric C Morales
(74) *Attorney, Agent, or Firm* — Faegre Drinker Biddle & Reath LLC

(57) ABSTRACT

An implantable medical device (IMD) includes a tap sensor configured to detect an impact event occurring on the surface of the patient's body. The tap sensor is configured to determine whether the impact event (which may be, for example, a tap of a finger or hand upon a surface of the body) likely is a communication directed at the tap sensor. In response to determining that the impact event likely is a communication directed at the tap sensor, the IMD is configured to transition from a first state to a second state.

10 Claims, 5 Drawing Sheets

(51) Int. Cl.
    *A61B 5/0402*    (2006.01)
    *A61B 5/0432*    (2006.01)

(56) References Cited

U.S. PATENT DOCUMENTS

| | | |
|---|---|---|
| 6,354,299 B1 | 3/2002 | Fischell et al. |
| 6,721,603 B2 | 4/2004 | Zabara et al. |
| 7,392,081 B2 | 6/2008 | Wagner et al. |
| 2003/0149459 A1* | 8/2003 | Von Arx ................. A61N 1/08 607/60 |
| 2004/0122489 A1 | 6/2004 | Mazar et al. |
| 2007/0060976 A1* | 3/2007 | Denzene ............ A61N 1/37252 607/60 |
| 2007/0078497 A1 | 4/2007 | Vandanacker |
| 2009/0105785 A1* | 4/2009 | Wei .................... A61N 1/36132 607/48 |
| 2009/0228073 A1 | 9/2009 | Scholten |
| 2009/0228079 A1 | 9/2009 | Libbus et al. |
| 2009/0248115 A1 | 10/2009 | Corndorf et al. |
| 2009/0270949 A1 | 10/2009 | Kalpin et al. |
| 2014/0085081 A1 | 3/2014 | Brown et al. |

OTHER PUBLICATIONS

PCT Invitation to Pay Additional Fees and Partial International Search Report issued in PCT/US2016/015990, dated May 21, 2016, 5 pages.

* cited by examiner

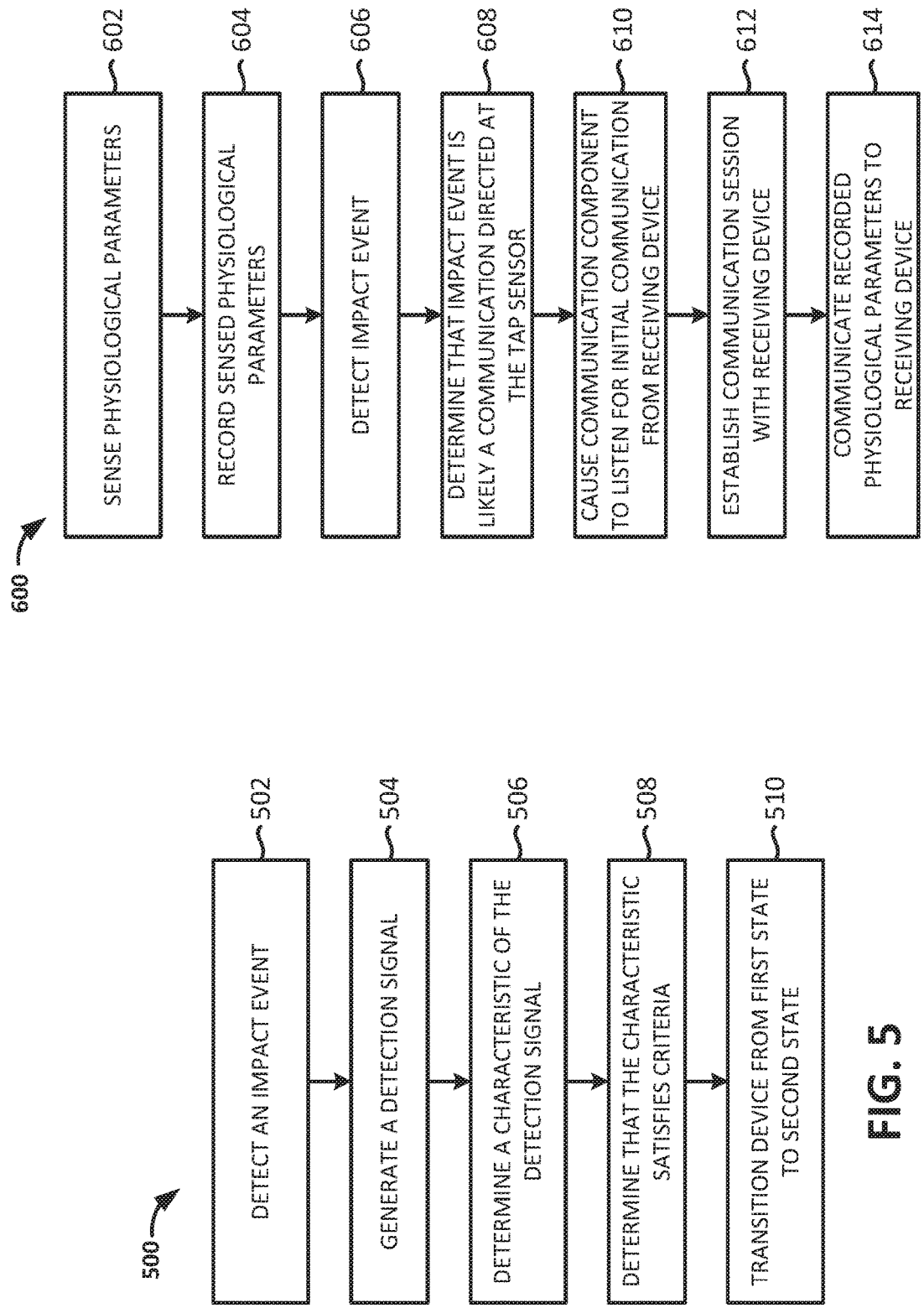

TAP SENSOR-ENABLED IMD

CROSS-REFERENCE TO RELATED APPLICATION

This application claims priority to Provisional Application No. 62/119,796, filed Feb. 23, 2015, which is herein incorporated by reference in its entirety.

TECHNICAL FIELD

Embodiments of the present invention relate to medical devices and systems for sensing physiological parameters and/or delivering therapy. More specifically, embodiments of the invention relate to devices and methods for communicating with an implantable medical device that includes a tap sensor.

BACKGROUND

Implantable medical devices (IMDs) may be configured to sense physiological parameters and/or provide therapy. Conventionally, devices such as programmers and wands have been used to cause IMDs to take various actions such as, for example, marking recordings of physiological parameters, initiating communications with other devices, and the like.

SUMMARY

Embodiments of the invention include an implantable medical device (IMD) having a tap sensor configured to detect an impact event occurring on the surface of the patient's body. In embodiments, the tap sensor is configured to determine whether the impact event (which may be, for example, a tap of a finger or hand upon a surface of the body) likely is a communication directed at the tap sensor. In response to determining that the impact event likely is a communication directed at the tap sensor, the IMD may be configured to transition from a first state to a second state.

In an Example 1, a system includes an implantable medical device configured to record a physiological parameter measurement. The implantable medical device includes a communication component configured to communicate the physiological parameter measurement to a receiving device; and a tap sensor configured to (1) detect an impact event on an external portion of the patient's body; and (2) in response to detecting the impact event, cause the communication component to transition from a first state, in which the communication component is dormant, to a second state, in which the communication component is configured to actively listen for incoming communication. The system may also include a receiving device configured to receive the physiological parameter measurement from the implantable medical device.

In an Example 2, the system of Example 1, wherein the implantable medical device comprises at least one of an implantable loop recorder (ILR), a cardiac pacemaker, an implantable cardioverter defibrillator (ICD) device, and a cardiac resynchronization therapy (CRT) device.

In an Example 3, the system of any of Examples 1 and 2, wherein the receiving device is an external device.

In an Example 4, the system of any of Examples 1-3, the tap sensor comprising at least one of an accelerometer and an inertial measurement unit (IMU).

In an Example 5, the system of any of Examples 1-4, wherein the physiological parameter measurement comprises a measurement of a cardiac activation signal.

In an Example 6, the system of any of Examples 1-5, wherein the tap sensor is further configured to determine whether the impact event likely comprises a communication directed at the tap sensor.

In an Example 7, the system of any of Examples 1-6, wherein the tap sensor comprises an impact event detector configured to detect the impact event and generate a detection signal in response thereto; and a processing unit configured to receive the detection signal from the impact event detector; determine at least one characteristic of the detection signal; and determine whether the at least one characteristic of the detection signal satisfies one or more criteria, wherein the impact event likely comprises a communication directed at the tap sensor if the at least one characteristic of the detection signal satisfies the one or more criteria.

In an Example 8, the system of Example 7, wherein the at least one characteristic is related to a force of the impact event.

In an Example 9, the system of any of Examples 7 and 8, wherein the at least one characteristic comprises a number of detected impact events occurring within a specified time period.

In an Example 10, an implantable medical device, configured to be implanted within a body of a patient, includes a sensing component configured to sense one or more physiological parameters; a memory configured to store the one or more physiological parameters; and a tap sensor configured to: detect an impact event on an external surface of the body of the patient; determine that the impact event likely comprises a communication directed at the tap sensor; and cause, in response to determining that the impact event likely comprises a communication directed at the tap sensor, the implantable medical device to be transitioned from a first state to a second state.

In an Example 11, the implantable medical device of Example 10, wherein the implantable medical device comprises at least one of an implantable loop recorder (ILR), a cardiac pacemaker, an implantable cardioverter defibrillator (ICD) device, and a cardiac resynchronization therapy (CRT) device.

In an Example 12, the implantable medical device of any of Examples 10 and 11, wherein the first state and the second state correspond to the sensing component, wherein: when the implantable medical device is in the first state, the sensing component does not sense the one or more physiological parameters; and when the implantable medical device is in the second state, the sensing component senses the one or more physiological parameters.

In an Example 13, the implantable medical device of any of Examples 10-12, further comprising a communication component configured to communicate the one or more physiological parameters to a receiving device, wherein the first state and the second state correspond to the communication component, wherein: when the implantable medical device is in the first state, the communication component is dormant; and when the implantable medical device transitions to the second state, the communication component begins listening for a communication from the receiving device.

In an Example 14, the implantable medical device of any of Examples 10-13, the tap sensor comprising: an impact event detector configured to detect the impact event and generate a detection signal in response thereto; and a processing component configured to: receive the detection signal from the impact event detector; determine at least one characteristic of the detection signal; and determine whether the at least one characteristic of the detection signal satisfies one or more criteria, wherein the processing component determines that the impact event likely comprises a communication directed at the tap sensor when the at least one characteristic of the detection signal satisfies the one or more criteria.

In an Example 15, the implantable medical device of any of Examples 10-14, the tap sensor comprising at least one of an accelerometer and an inertial measurement unit (IMU).

In an Example 16, a system includes an implantable medical device configured to record a physiological parameter measurement, the implantable medical device: a communication component configured to communicate the physiological parameter measurement to a receiving device; and a tap sensor configured to (1) detect an impact event on an external portion of the patient's body; and (2) in response to detecting the impact event, cause the communication component to transition from a first state, in which the communication component is dormant, to a second state, in which the communication component is configured to actively listen for incoming communication. The system also includes a receiving device configured to receive the physiological parameter measurement from the implantable medical device.

In an Example 17, the system of Example 16, wherein the implantable medical device comprises at least one of an implantable loop recorder (ILR), a cardiac pacemaker, an implantable cardioverter defibrillator (ICD) device, and a cardiac resynchronization therapy (CRT) device.

In an Example 18, the system of Example 16, wherein the receiving device is an external device.

In an Example 19, the system of Example 16, the tap sensor comprising at least one of an accelerometer and an inertial measurement unit (IMU).

In an Example 20, the system of Example 16, wherein the physiological parameter measurement comprises a measurement of a cardiac activation signal.

In an Example 21, the system of Example 16, wherein the tap sensor is further configured to determine whether the impact event likely comprises a communication directed at the tap sensor.

In an Example 22, system of Example 21, wherein the tap sensor comprises: an impact event detector configured to detect the impact event and generate a detection signal in response thereto; and a processing unit configured to: receive the detection signal from the impact event detector; determine at least one characteristic of the detection signal; and determine whether the at least one characteristic of the detection signal satisfies one or more criteria, wherein the impact event likely comprises a communication directed at the tap sensor if the at least one characteristic of the detection signal satisfies the one or more criteria.

In an Example 23, the system of Example 22, wherein the at least one characteristic is related to a force of the impact event.

In an Example 24, the system of Example 22, wherein the at least one characteristic comprises a number of detected impact events occurring within a specified time period.

In an Example 25, an implantable medical device, configured to be implanted within a body of a patient, comprises a sensing component configured to sense one or more physiological parameters; a memory configured to store the one or more physiological parameters; and a tap sensor configured to: detect an impact event on an external surface of the body of the patient; determine that the impact event likely comprises a communication directed at the tap sensor; and cause, in response to determining that the impact event likely comprises a communication directed at the tap sensor, the implantable medical device to be transitioned from a first state to a second state.

In an Example 26, the implantable medical device of Example 25, wherein the implantable medical device comprises at least one of an implantable loop recorder (ILR), a cardiac pacemaker, an implantable cardioverter defibrillator (ICD) device, and a cardiac resynchronization therapy (CRT) device.

In an Example 27, the implantable medical device of Example 25, wherein the first state and the second state correspond to the sensing component, wherein: when the implantable medical device is in the first state, the sensing component does not sense the one or more physiological parameters; and when the implantable medical device is in the second state, the sensing component senses the one or more physiological parameters.

In an Example 28, the implantable medical device of Example 25, further comprising a communication component configured to communicate the one or more physiological parameters to a receiving device, wherein the first state and the second state correspond to the communication component, wherein: when the implantable medical device is in the first state, the communication component is dormant; and when the implantable medical device transitions to the second state, the communication component begins listening for a communication from the receiving device.

In an Example 29, the implantable medical device of Example 25, the tap sensor comprising: an impact event detector configured to detect the impact event and generate a detection signal in response thereto; and a processing component configured to: receive the detection signal from the impact event detector; determine at least one characteristic of the detection signal; and determine whether the at least one characteristic of the detection signal satisfies one or more criteria, wherein the processing component determines that the impact event likely comprises a communication directed at the tap sensor when the at least one characteristic of the detection signal satisfies the one or more criteria.

In an Example 30, the implantable medical device of Example 29, wherein the at least one characteristic of the detection signal is related to an amount of force associated with the impact event.

In an Example 31, the implantable medical device of Example 25, the tap sensor comprising at least one of an accelerometer and an inertial measurement unit (IMU).

In an Example 32, the implantable medical device of Example 25, wherein the tap sensor is activated and deactivated based on a pulse width modulation (PWM) cycle.

In an Example 33, a method of facilitating communication between an implantable medical device and a receiving device, the implantable medical device configured to be implanted within a body of a patient, comprises: detecting, using a tap sensor, an impact event, wherein the impact event comprises an impact of an object with an external surface of the body of the patient; determining that the impact event likely comprises a communication directed at the tap sensor; and causing, in response to determining that the impact event likely comprises a communication directed at the tap sensor, a communication component to transition from a first state to a second state, wherein, in the second state, the communication component is configured to listen for communications from the receiving device.

In an Example 34, the method of Example 33, further comprising: sensing a plurality of cardiac measurements;

recording the plurality of cardiac measurements; detecting an initial communication from the receiving device to the communication component; in response to detecting the initial communication, establishing a communication session with the receiving device; and communicating the plurality of cardiac measurements to the receiving device.

In an Example 35, the method of Example 33, wherein determining that the impact event likely comprises a communication directed at the tap sensor comprises: detecting, using an impact event detector, the impact event; generating, in response to detecting the impact event, a detection signal; determining at least one characteristic of the detection signal; and determining whether the at least one characteristic of the detection signal satisfies one or more criteria.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 5 is a flow diagram depicting an illustrative method of communicating with an IMD, in accordance with embodiments of the invention.

FIG. 6 is a flow diagram depicting an illustrative method of facilitating communication between an implantable medical device and a receiving device, in accordance with embodiments of the invention.

Figure 1:
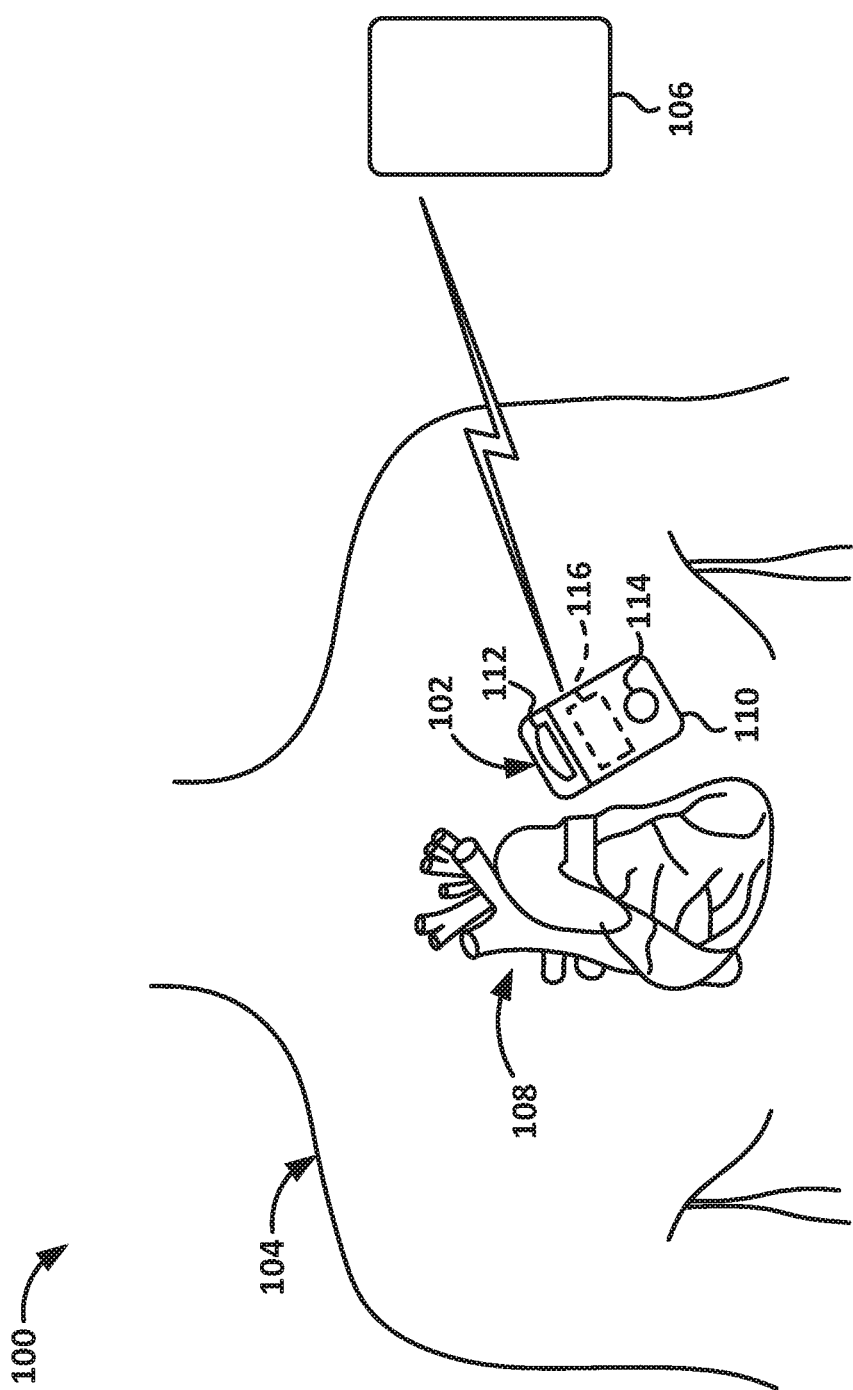
FIG. 1 is a schematic illustration of a system having an implantable cardiac monitor and a receiving device, in accordance with embodiments of the invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic illustration of an implantable system 100 including an implantable medical device (IMD) 102 implanted within a patient's body 104 and configured to communicate with a receiving device 106. In embodiments, the IMD 102 may be implanted subcutaneously within an implantation location or pocket in the patient's chest or abdomen and may be configured to monitor (e.g., sense and/or record) physiological parameters associated with the patient's heart 108. In embodiments, the IMD 102 may be an implantable cardiac monitor (ICM) (e.g., an implantable loop recorder (ILR)) configured to record physiological parameters such as, for example, one or more cardiac activation signals, heart sounds, blood pressure measurements, oxygen saturations, and/or the like. In embodiments, the IMD 102 may be configured to monitor physiological parameters that may include one or more signals indicative of a patient's physical activity level and/or metabolic level, such as an acceleration signal. In embodiments, the IMD 102 may be configured to monitor physiological parameters associated with one or more other organs, systems, and/or the like. The IMD 102 may be configured to sense and/or record at regular intervals, continuously, and/or in response to a detected event. In embodiments, such a detected event may be detected by one or more sensors of the IMD 102, another IMD (not shown), an external device (e.g., the receiving device 106), and/or the like.

For purposes of illustration, and not of limitation, various embodiments of devices that may be used to record physiological parameters in accordance with present invention are described herein in the context of IMDs that may be implanted under the skin in the chest region of a patient. An IMD may, for example, be implanted subcutaneously such that all or selected elements of the device are positioned on the patient's front, back, side, or other body location suitable for sensing cardiac activity and/or other physiological parameters, and/or delivering cardiac stimulation therapy and/or other therapies. It is understood that elements of the IMD may be located at several different body locations, such as in the chest, abdominal, or subclavian region with electrode elements respectively positioned at different regions near, around, in, or on the heart and/or other organs.

In embodiments, the primary housing (e.g., the active or non-active can) of the IMD, for example, may be configured for positioning outside of the rib cage at an intercostal or subcostal location, within the abdomen, or in the upper chest region (e.g., subclavian location, such as above the third rib). In embodiments, one or more leads incorporating electrodes may be located in direct contact with the heart, great vessel or coronary vasculature, such as via one or more leads implanted by use of conventional transveous delivery approaches. In embodiments, one or more electrodes may be located on the primary housing and/or at other locations about, but not in direct contact with the heart, great vessel or coronary vasculature. According to embodiments, for example, one or more electrode subsystems or electrode arrays may be used to sense cardiac activity and/or deliver cardiac stimulation energy in an IMD configuration employing an active can or a configuration employing a non-active can. Electrodes may be, for example, situated at anterior and/or posterior locations relative to the heart.

In the embodiment illustrated in FIG. 1, the IMD 102 is an implantable loop recorder (ILR). As shown, the IMD 102 may include a housing 110 and two electrodes 112 and 114 coupled thereto. According to embodiments, the IMD 102 may include any number of electrodes (and/or other types of sensors such as, e.g., thermometers, barometers, pressure sensors, optical sensors, motion sensors, and/or the like) in any number of various types of configurations, and the housing 108 may include any number of different shapes, sizes, and/or features. In embodiments, the IMD 102 may be configured to sense physiological parameters and record the physiological parameters. For example, the IMD 102 may be configured to activate (e.g., periodically, continuously, upon detection of an event, and/or the like), record a specified amount of data (e.g., physiological parameters) in a memory and communicate that recorded data to a receiving device 106. For example, in the case of an ILR, the IMD 102 may activate, record cardiac signals for a certain period of time, deactivate, and activate to communicate the recorded signals to the receiving device 106.

In accordance with embodiments of the invention, an IMD may be implemented to include an electrode system that provides for one or both of cardiac sensing and arrhythmia therapy delivery. According to embodiments, an IMD may be implemented as a chronically implantable system that performs monitoring, diagnostic and/or therapeutic functions. The IMD may automatically detect and/or treat cardiac arrhythmias. In embodiments, the IMD may include a pulse generator and three or more electrodes that are implanted subcutaneously in the chest region of the body, such as in the anterior thoracic region of the body. The IMD may be used to provide atrial and/or ventricular therapy for bradycardia and tachycardia arrhythmias. Tachyarrhythmia therapy may include cardioversion, defibrillation and anti-tachycardia pacing (ATP), for example, to treat atrial or ventricular tachycardia or fibrillation. Bradycardia therapy may include temporary post-shock pacing for bradycardia or asystole. Methods and systems for implementing post-shock pacing for bradycardia or asystole are described in commonly owned U.S. Pat. No. 7,392,081, which is hereby incorporated herein by reference in its entirety for all purposes.

The IMD may be configured to detect a variety of physiological signals that may be used in connection with various diagnostic, therapeutic and/or monitoring implementations. For example, the IMD may include sensors or circuitry for detecting respiratory system signals, cardiac system signals, and/or signals related to patient activity. In embodiments, the IMD may be configured to sense intrathoracic impedance, from which various respiratory parameters may be derived, including, for example, respiratory tidal volume and minute ventilation. Sensors and associated circuitry may be incorporated in connection with a IMD for detecting one or more body movement or body posture and/or position related signals. For example, accelerometers and/or GPS devices may be employed to detect patient activity, patient location, body orientation, and/or torso position.

In various embodiments, the receiving device 106 may be, for example, a programmer, controller, patient monitoring system, and/or the like. Although illustrated, in FIG. 1, as an external device, the receiving device 106 may include an implantable device configured to communicate with the IMD 102 that may, for example, be a control device, another monitoring device, a pacemaker, an implantable defibrillator, a cardiac resynchronization therapy (CRT) device and/or the like, and may be an implantable medical device known in the art or later developed, for providing therapy and/or diagnostic data about the patient and/or the IMD 102. In various embodiments, the IMD 102 may be a pacemaker, an implantable cardioverter defibrillator (ICD) device, or a cardiac resynchronization therapy (CRT) device. In various embodiments, the IMD 102 may include both defibrillation and pacing/CRT capabilities (e.g., a CRT-D device).

The system 100 may be used to implement coordinated patient measuring and/or monitoring, diagnosis, and/or therapy in accordance with embodiments of the invention. The system 100 may include, for example, one or more patient-internal medical devices, such as an IMD 102, and one or more patient-external medical devices, such as receiving device 106. In embodiments, the receiving device 106 may be configured to perform monitoring, and/or diagnosis and/or therapy functions external to the patient (i.e., not invasively implanted within the patient's body). The receiving device 106 may be positioned on the patient, near the patient, or in any location external to the patient.

As shown in FIG. 1, the IMD 102 may include a tap sensor 116 that may be used to allow a physician, clinician, and/or patient to manually trigger and/or transfer information to the IMD 102 and/or receiving device 106. For example, the patient may trigger the tap sensor 116 upon perceiving a cardiac event. The tap sensor 116 may then initiate the recording of cardiac signals and/or other sensor signals in the IMD 102. Later, a clinician may trigger the tap sensor 116, initiating the transfer of the recorded cardiac and/or other signals from the IMD 102 to the receiving device 106 for display and/or diagnosis. The tap sensor 116 may also be used by the patient, clinician, and/or physician as an activation stimulus to the IMD 102 to update and/or select a stimulation vector or other therapy and/or sensing parameter.

In embodiments, the IMD 102 and the receiving device 106 may communicate through a wireless link. For example, the IMD 102 and the receiving device 106 may be coupled through a short-range radio link, such as Bluetooth, IEEE 802.11, and/or a proprietary wireless protocol. The communications link may facilitate uni-directional or bi-directional communication between the IMD 102 and the receiving device 106. Data and/or control signals may be transmitted between the IMD 102 and the receiving device 106 to coordinate the functions of the IMD 102 and the receiving device 106. In embodiments, patient data may be downloaded from one or more of the IMD 102 and the receiving device 106 periodically or on command. The physician and/or the patient may communicate with the IMD 102 and the receiving device 106, for example, to acquire patient data or to initiate, terminate or modify recording and/or therapy.

The illustrative system 100 shown in FIG. 1 is not intended to suggest any limitation as to the scope of use or functionality of embodiments of the invention disclosed throughout this document. Neither should the illustrative system 100 be interpreted as having any dependency or requirement related to any single component or combination of components illustrated therein. For example, in embodiments, the illustrative system 100 may include additional components. Additionally, any one or more of the components depicted in FIG. 1 can be, in embodiments, integrated with various ones of the other components depicted therein (and/or components not illustrated). Any number of other components or combinations of components can be integrated with the illustrative system 100 depicted in FIG. 1, all of which are considered to be within the ambit of this disclosure.

Figure 2:
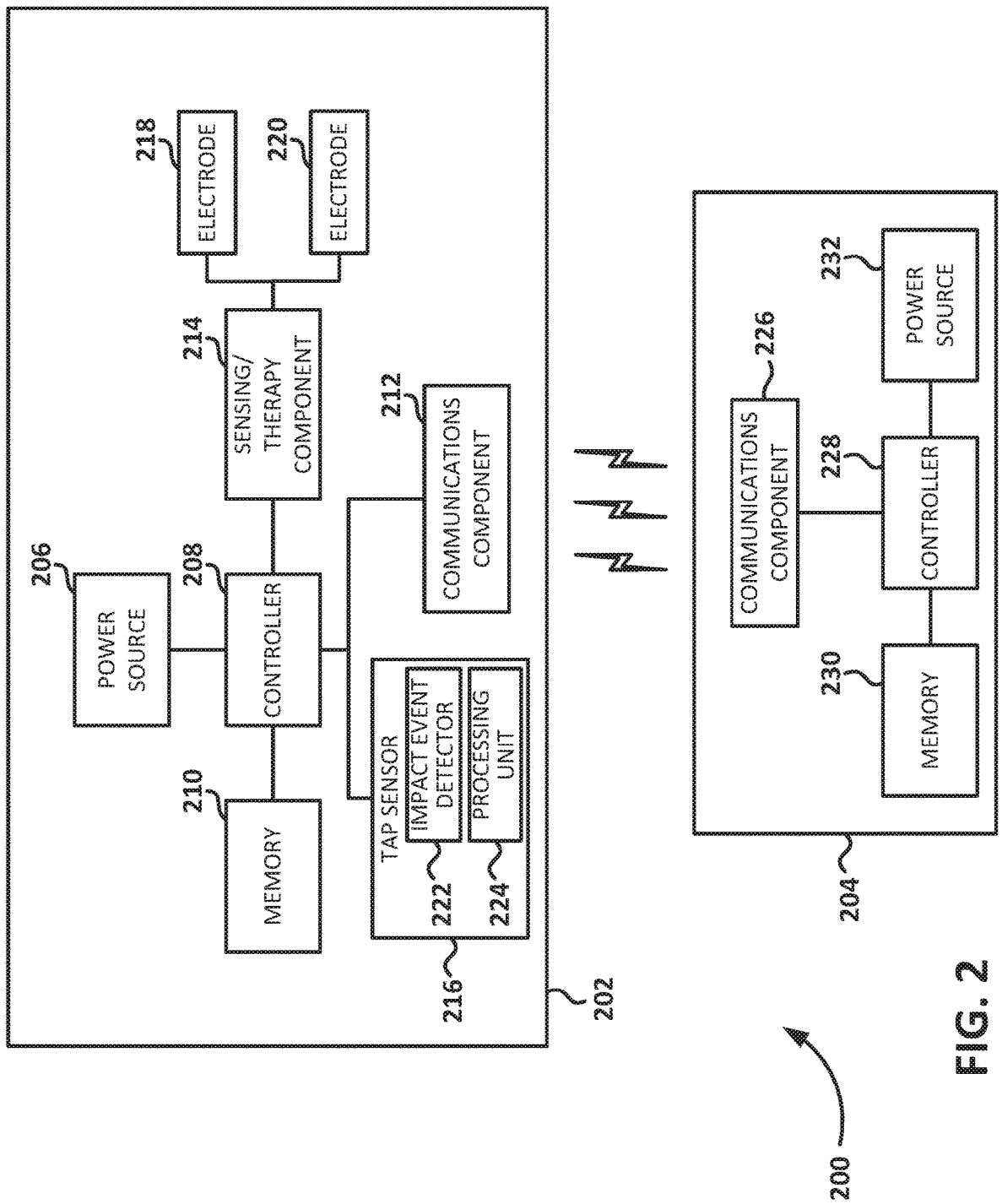
FIG. 2 is a schematic block diagram of an implantable system having an IMD and a receiving device, in accordance with embodiments of the invention.

FIG. 2 is a block schematic diagram of a system 200 including an IMD 202 (such as, e.g., the IMD 102 depicted in FIG. 1) and a receiving device 204 (such as, e.g., the receiving device 106 depicted in FIG. 1). As illustrated in FIG. 2, the IMD 202 includes a power source 206 that provides electrical energy to a number of other components, including a controller 208, a memory 210, a communications component 212, a sensing/therapy component 214, and a tap sensor 216. In embodiments, the sensing/therapy component 214 is coupled to electrodes 218 and 220 and may be configured to receive detected signals from the electrodes, provide stimulation energy to the electrodes, and/or the like. According to embodiments, the IMD 202 may include more than two electrodes. According to embodiments, the power source 206 may include one or more batteries, capacitors, and/or the like.

The controller 208 may include, for example, a processing unit, a pulse generator, and/or the like. The controller 208 may be a programmable micro-controller or microprocessor, and may include one or more programmable logic devices (PLDs) or application specific integrated circuits (ASICs). The controller 208 may execute instructions and perform desired tasks as specified by the instructions. The controller may also be configured to store information in the memory 210 and/or access information from the memory 210. The memory 210 may include volatile and/or non-volatile memory, and may store instructions that, when executed by the controller 208 cause methods and processes to be performed by the IMD 202. For example, in embodiments, the controller 208 may process instructions and/or data stored in the memory 210 to control delivery of an electrical stimulation therapy by the IMD 202. In embodiments, the controller 208 may receive sensed physiological parameters via the electrodes 218 and 220 (and/or other sensors) and store the sensed physiological parameters in the memory 210. In embodiments, the controller 208 may be configured to access stored physiological parameters from the memory 210 and analyze the physiological parameters, cause the communications component 212 to communicate the physiological parameters to the receiving device, and/or the like.

The sensing/therapy component 214 may be, or include, hardware, firmware, and/or software configured to sense physiological parameters and/or provide therapy. Information from sensing circuits included in the sensing/therapy component 214 may be used, e.g., to diagnose physiological conditions, adjust pacing and/or communications parameters, and/or the like. In embodiments, the sense circuits may amplify and filter signals sensed from sensors positioned in the right or left atrium, in the right or left ventricle, and/or from sensors on an external surface of the pacing controller. The sense circuits may include one or more A/D converters. The sensors (which may be, or include, the electrodes 218 and 220) may be attached to leads implanted within, on, or near the heart, and in some implementations the IMD 202 may communicate sensed information to the receiving device 202 directly or through a lead that includes a receiver. The sensing/therapy component 214 of the IMD 202 may include, for example, one or more can or housing electrodes disposed on an exterior surface of the IMD 202.

The tap sensor 216 may be configured to detect an impact event on an external portion of the patient's body and, in response to detecting the impact event, cause the IMD 202 to transition from a first state to a second state. An impact event may include any type of contact with an external surface of the patient's body such as, for example, a tap of a finger on the patient's abdomen. In embodiments, the tap sensor causes the IMD 202 to transition from a first state to a second state by communicating a detection signal to the controller 208, which transitions the IMD 202 from the first state to the second state. In embodiments, the first and/or second states of the IMD 202 may correspond to any one or more of the components illustrated in FIG. 2, components not illustrated in FIG. 2, aspects of embodiments of functionalities of one or more of the aforementioned components, and/or the like.

For example, in embodiments, the controller 208 may be configured to cause the communication component 212 to transition from a first state, in which the communication component 212 is dormant, to a second state, in which the communication component 212 is configured to actively listen for incoming communication (e.g., from the receiving device 204). For example, embodiments of the tap sensor 216 may be used to activate the communications component 212, which may then be ready to establish a communication session with the receiving device 204 so that recorded physiological parameters may be communicated to the receiving device 204. In this manner, embodiments of the invention facilitate saving more energy (e.g., power from the power source 204) than conventional IMDs, which are often configured to immediately attempt to transmit data to a receiving device upon receiving an external user input. In embodiments, the tap sensor 216 may be configured to cause the sensing/therapy component 214 to transition from a first state, in which the sensing/therapy component 214 is dormant, to a second state, in which the sensing/therapy component 214 is activated. Any number of other states of the IMD 202 may activated, deactivated, and/or the like in response to a detection of an external impact event by the tap sensor 216.

According to embodiments, as shown in FIG. 2, the tap sensor 216 may include an impact event detector 222 configured to detect an impact event and, in response to detecting the impact event, generate a detection signal. The impact event detector 222 may provide the detection signal to a processing unit 224 that is configured to analyze the detection signal. According to embodiments, the impact event detector may be, or include, for example, an accelerometer, an inertial measurement unit (IMU), an acoustic transducer, and/or the like, and may be configured to detect impact events associated with an external surface of the patient's body by analyzing data associated with vibrations, sound, gravity, and/or the like. The processing unit 224 may be, or include, a processor, digital signal processor (DSP), logical circuitry, and/or the like. In embodiments, the processing unit 224 may be, or include, hardware, firmware, and/or software that is part of the controller 208, stored within the memory 210, and/or the like.

For example, in embodiments, the processing unit may be configured to receive the detection signal from the impact event detector, determine one or more characteristics of the detection signal, and determine whether the one or more characteristics of the detection signal satisfy one or more criteria. In embodiments, the processing unit may be configured to determine whether the impact event likely comprises a communication directed at the tap sensor. For example, the processing unit may determine that the impact event likely comprises a communication directed at the tap sensor if the one or more characteristics of the detection signal satisfy the one or more criteria. According to embodiments, characteristics of the detection signal may be related to any number of different aspects of the impact event such as, for example, a force of the impact event, an origination location of the impact event, a number of detected impact events occurring within a specified time period, and/or the like.

For example, the processing unit 224 may be configured to analyze a detection signal received from an impact event detector 222 to determine a characteristic related to a force of the impact event such as, for example, an amount (e.g., amplitude) of force with which the impacting object impacted the surface of the patient's body, a duration of application of force upon the surface of the patient's body, a momentum associated with the impacting object, an impulse (i.e., the force of impact multiplied by the time over which it acts), and/or the like. In this manner, the processing unit 224 of the tap sensor 216 may be able to differentiate between different types of impact events. In embodiments, the processing unit 224 may analyze a detection signal to determine whether a characteristic of a force related to the impact event satisfies one or more criteria such as, for example, a designated range, threshold, and/or the like. For example, an impact event may be determined to likely be a communication directed at the tap sensor if the amplitude of the force related to the impact event is above a specified threshold, below a specified threshold, and/or within a specified range. According to embodiments, any number of different types of characteristics of a detection signal may be used, in conjunction with any number of different types of criteria, to ascertain information about impact events.

Using specified criteria, the processing unit 224 can be configured to differentiate between impact events that represent intentional actions to cause the IMD 202 to transition from a first state to a second state and impact events that may be accidental, or otherwise natural, occurrences such as, for example, heart beats, impacts with the ground as a result of the patient falling, impacts with objects as a result of the patient accidentally running into them, vibrations and other measurable changes caused by the patient running (e.g., impacts between the patient's feet and the ground), impacts caused by sound waves impinging on the surface of the patient's body (e.g., at concerts, in theaters, etc.), and/or the like.

In embodiments, criteria may also be configured to enable the processing unit 224 to differentiate between different commands. For example, different amounts of force intentionally applied by a user (e.g., a patient, clinician, etc.), different numbers of taps, different locations of taps, and/or the like may be recognized by the processing unit 224 as representing different commands. That is, for example, a user may tap on the patient's body with a first amount of force, at a first location, and/or a first number of times (e.g., within a specified time period) to cause the IMD 202 to begin to record physiological parameters, and the user may tap on the patient's body with a second amount of force, at a second location, and/or a second number of times to cause communication component 212 of the IMD 202 to activate and begin listening for initial communications from the receiving device 204.

According to embodiments, any number of different criteria may be used to configure the tap sensor to identify different types of commands communicated using impact events. For example, different tap patterns (e.g., combinations of numbers of taps, pauses, time between taps, etc.) may be used to represent different types of commands; different characteristics related to force may be used to represent different types of commands; tapping on different impact event origination locations (e.g., different locations on the surface of the patient's body) may be used to represent different types of commands; and/or the like. In embodiments, combinations of different characteristics may be used to distinguish between different commands. In embodiments, any number of different commands may be represented using characteristics of detection signals corresponding to detected impact events. For example, impact events may be used to select physiological parameters to be monitored, activate/deactivate recording features, select durations for recording physiological parameters, begin recording one or more physiological parameters for a specified duration of time, activate aspects of communications components, send communications, add markers to ECGs as they're being recorded, and/or the like.

According to embodiments, the processing unit 224 may be configured to modify the one or more criteria that it uses to determine whether detected impact events are likely to be communications directed at the tap sensor 216, differentiate between different commands based on characteristics of the detection signals, and/or the like. In embodiments, the processing unit 224 may be configured to modify the methods used for applying the criteria (e.g., for analyzing detection signals), and/or the like. For example, the processing unit 224 may employ a supervised and/or unsupervised machine learning technique to modify its functionality.

In embodiments, for example, the processing unit 224 may be configured to cause the communications component 212 to begin listening for initial communications from the receiving device 204 in response to detecting an impact event and determining that the detected impact event is likely a communication directed at the tap sensor 216. Upon receiving an initial communication from the receiving device 204, the communications component 212 may be configured to provide an indication of the receipt of that initial communication to the processing unit 224. The processing unit 224 may correlate the indication of the receipt of the initial communication with one or more characteristics of the detection signal corresponding to the detected impact event. Similarly, the processing unit 224 may correlate an indication of the lack of receipt of an initial communication from the receiving device 204 with one or more characteristics of a detection signal corresponding to a detected impact event after which the communications component 212 did not receive an initial communication from the receiving device 204. The processing unit 224 may use the indications and correlated detection signals (and/or characteristics thereof) as inputs to a machine learning technique that facilitates improving criteria, analyses, and/or the like for differentiating between different types of impact events, commands, and/or the like. In embodiments, any number of other types of feedback may be used to facilitate any number of different types of machine learning techniques for improving the functionality of the tap sensor 216.

As shown in FIG. 2, the receiving device 204 includes a communications component 226 having circuits and one or more transmitters and/or receivers for communicating wirelessly with the IMD 202. Similarly, the communications component 212 of the IMD 202 is configured to communicate, via the communications component 226, with the receiving device 204, which may include one or more implantable co-implanted devices and/or one or more external devices (e.g., the external device 106 depicted in FIG. 1). For example, the communications component 212 of the IMD 202 may be configured to communicate one or more physiological parameters to the receiving device 204. In embodiments, the communications component 212 may also facilitate communications with other IMDs 202 such as, for example, to facilitate coordinated operations between the IMDs. By way of example, the IMD 202 may communicate with a patient-worn, portable or bedside communication system via the communications component 212. In embodiments, one or more physiologic or non-physiologic sensors (subcutaneous, cutaneous, or external of patient) may be equipped with a short-range wireless communication interface, such as an interface conforming to a known communications standard, such as Bluetooth or IEEE 802 standards. Data acquired by such sensors may be communicated to the IMD 202 via the communications component 212. It is also noted that physiologic or non-physiologic sensors equipped with wireless transmitters or transceivers may communicate with a receiving system external of the patient (e.g., the receiving device 204 and/or the receiving device 106 depicted in FIG. 1).

According to various embodiments, the communications component 212 may include one or more transmitters, receivers, transceivers, transducers, and/or the like, and may be configured to facilitate any number of different types of wireless communication such as, for example, radio-frequency (RF) communication, microwave communication, infrared communication, acoustic communication, inductive communication, conductive communication, and/or the like. The communications component 226 may, in addition to facilitating wireless (e.g., RF, microwave, acoustic, etc.) communication with the IMD 202, facilitate wireless communication with an external device, such as a programming device, such that information may be provided to the receiving device 204 or supplied to the external device. In embodiments, the communications component 226 may include an antenna disposed on or in the additional device 204 or on a distal portion of an attached lead (not shown).

In an implementation, the receiving device 204 includes a controller 228 that may include, for example, a processing unit, a pulse generator, and/or the like. The controller 228 may be a programmable micro-controller or microprocessor, and may include one or more programmable logic devices (PLDs) or application specific integrated circuits (ASICs). The controller 228 may execute instructions and perform desired tasks as specified by the instructions. The controller may also be configured to store information in the memory 230 and/or access information from the memory 230. The memory 230 may include volatile and/or non-volatile memory, and may store instructions that, when executed by the controller 228 cause methods and processes to be performed by the receiving device 204. The receiving device 204 may also include a power source 232 that supplies power to the circuits and components of the receiving device 204.

The illustrative system 200 shown in FIG. 2 is not intended to suggest any limitation as to the scope of use or functionality of embodiments of the invention disclosed throughout this document. Neither should the illustrative system 200 be interpreted as having any dependency or requirement related to any single component or combination of components illustrated therein. For example, in embodiments, the illustrative system 200 may include additional components. Additionally, any one or more of the components depicted in FIG. 2 can be, in embodiments, integrated with various ones of the other components depicted therein (and/or components not illustrated). Any number of other components or combinations of components can be integrated with the illustrative system 200 depicted in FIG. 2, all of which are considered to be within the ambit of this disclosure.

Figure 3:
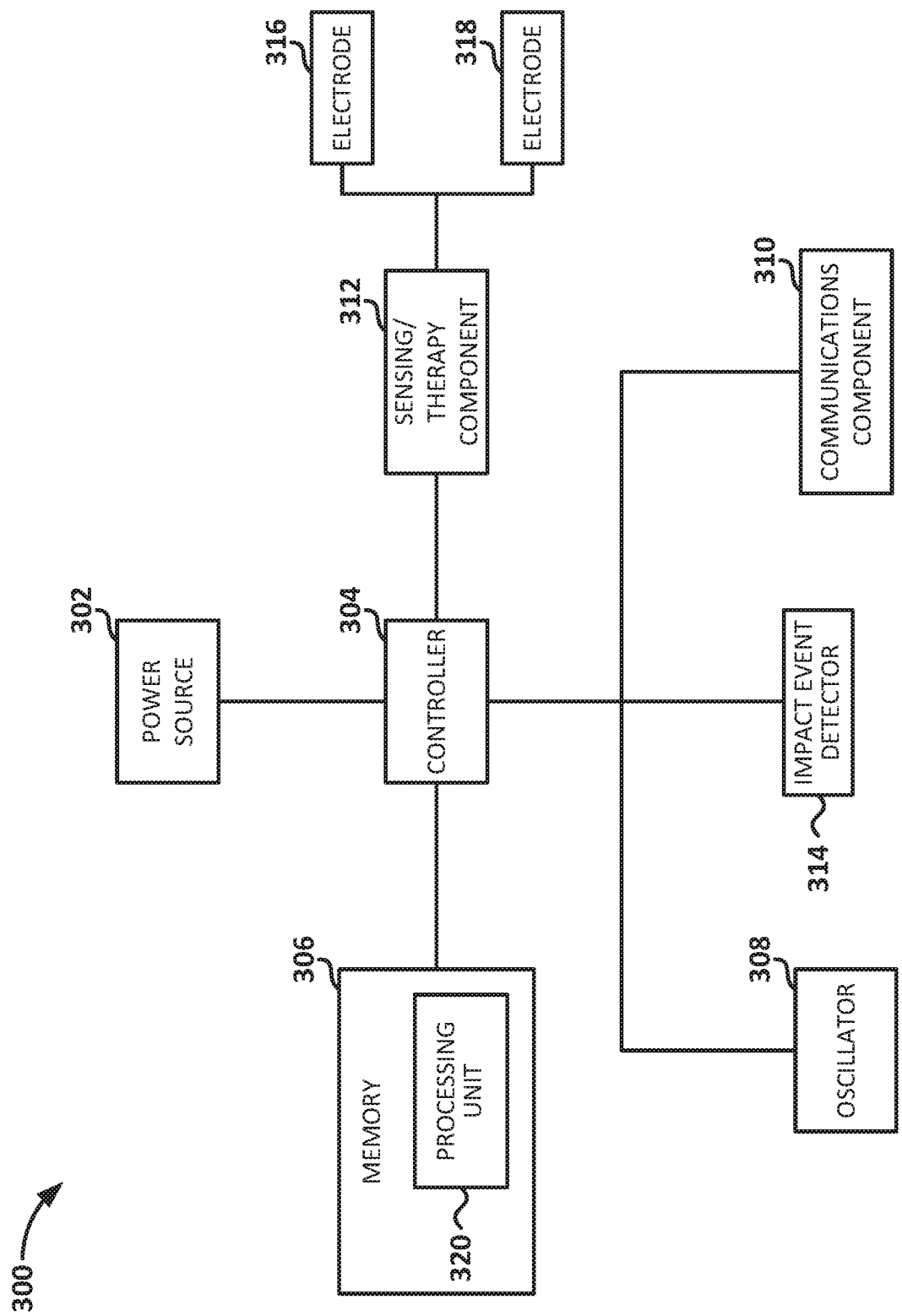
FIG. 3 is a schematic block diagram of an IMD, in accordance with embodiments of the invention.

FIG. 3 is a schematic block diagram of an IMD 300 illustrating aspects of embodiments of the invention. As shown in FIG. 3, the IMD 300 includes a power source 302 that powers a controller 304 coupled to a memory 306. An oscillator 308 coupled to the controller 304 may be used as a clocking mechanism to provide timing functions to the controller 304. In embodiments, other types of clocking mechanisms may be used as well as, or in addition, to the oscillator 308. The IMD 300 also includes a communications component 310, a sensing/therapy component 312, and an impact event detector 314. As shown in FIG. 3, the sensing/therapy circuit 314 may be coupled to electrodes 316 and 318 and is configured to receive sensed signals from the electrodes. According to embodiments, the IMD 300 may include more than two electrodes, the sensing/therapy component 312 may be coupled to other types of sensors, and/or the like. In embodiments, the communications component 310 may be similar to the communications component 210 depicted in FIG. 2 and may include a transceiver and an antenna. In embodiments, any number of the components illustrated in FIG. 3 may be, include, or be similar to, similarly named components depicted in FIG. 2.

The illustrative IMD 300 shown in FIG. 3 is not intended to suggest any limitation as to the scope of use or functionality of embodiments of the invention disclosed throughout this document. Neither should the illustrative IMD 300 be interpreted as having any dependency or requirement related to any single component or combination of components illustrated therein. For example, in embodiments, the illustrative IMD 300 may include additional components. Additionally, any one or more of the components depicted in FIG. 3 can be, in embodiments, integrated with various ones of the other components depicted therein (and/or components not illustrated). Any number of other components or combinations of components can be integrated with the illustrative IMD 300 depicted in FIG. 3, all of which are considered to be within the ambit of this disclosure.

In the embodiments depicted in FIG. 3, the memory 306 includes a processing unit 320 that may be, or include, one or more computer-executable instructions configured to be executed by the controller 304 to perform, for example, one or more of the functions of a tap sensor as described herein. In embodiments, the impact event detector 314 and the processing unit 320 (e.g., as executed by the controller 304) are, together, a tap sensor (e.g., the tap sensor 216 depicted in FIG. 2). The oscillator 308, and/or other timing component, may be used for timing functions associated with the controller 304. In embodiments, the controller 304 may utilize timing functions to control the operation of the tap sensor (e.g., the impact event detector 314 and/or processing unit 320). For example, the controller 304 may cause the impact event detector 314 to activate and deactivate periodically and may use, for example, a pulse width modulation (PWM) scheme to schedule the activation/deactivation of the impact event detector 314.

Figure 4:
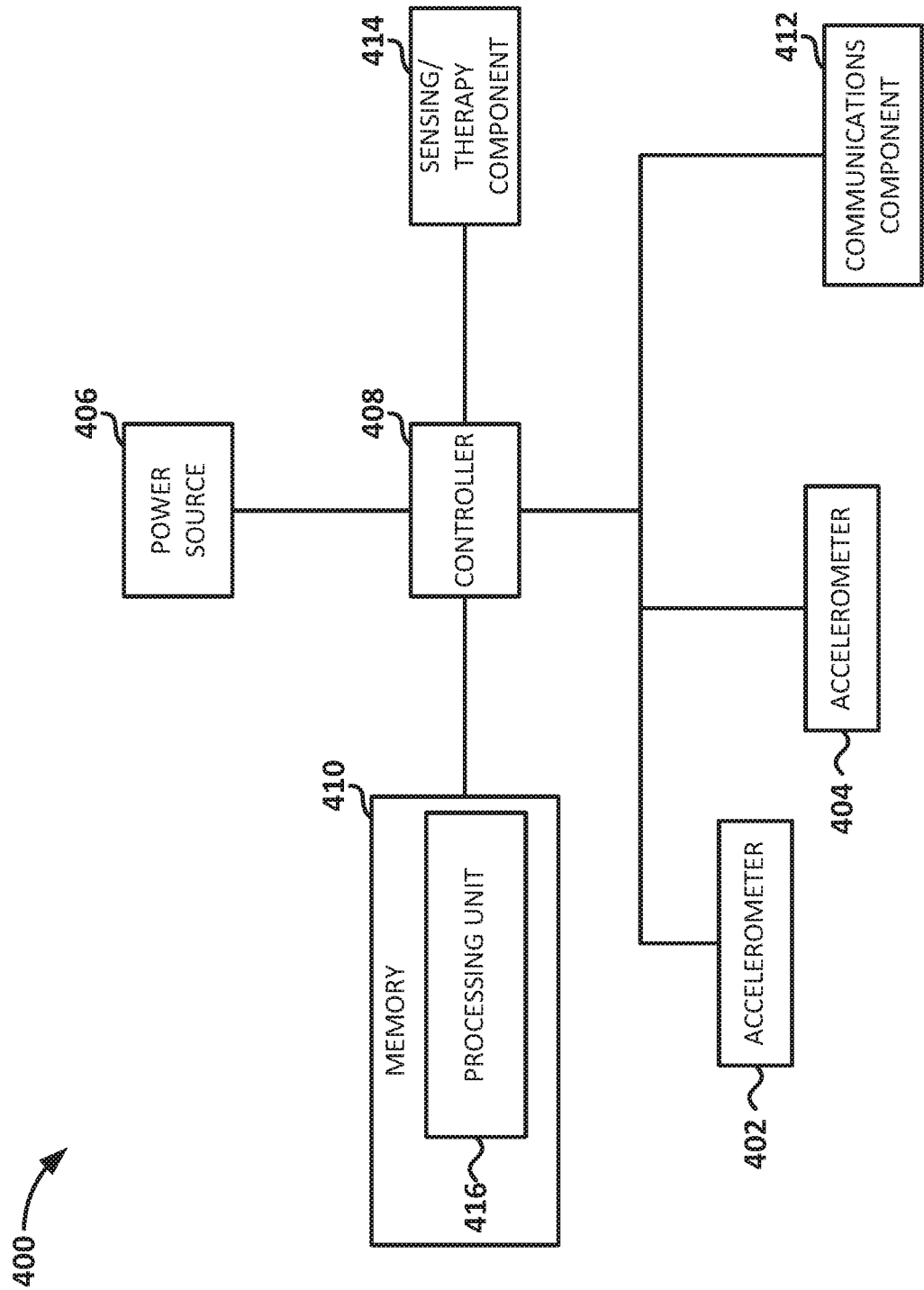
FIG. 4 is a schematic block diagram of an IMD, in accordance with embodiments of the invention.

In embodiments, the memory 306 (and/or any other memory depicted herein such as, for example, the memory 210 depicted in FIG. 2, and/or the memory 410 depicted in FIG. 4) may include computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; or any other medium that can be used to store information and can be accessed by a computing device (e.g., a controller 304 which may be, or include, a processor) such as, for example, quantum state memory, and the like.

In embodiments, the memory 306 stores computer-executable instructions that, when executed by the controller 304, cause the controller 304 to implement aspects of embodiments of system components and/or to perform aspects of embodiments of methods and procedures discussed herein. Computer-executable instructions may include, for example, computer code, machine-useable instructions, and the like such as, for example, program components capable of being executed by one or more processors. Examples of such program components include a processing unit 320. Program components may be programmed using any number of different programming environments, including various languages, development kits, frameworks, and/or the like. Some or all of the functionality contemplated herein may also be implemented in hardware and/or firmware.

In embodiments, the impact event detector 314 may have uses other than for detecting impact events for transitioning from a first state to a second state. For example, the impact event detector may be, or include, an accelerometer (e.g., a 3-axis accelerometer) that may be used by the IMD 300 to detect physiological parameters such as, for example, patient posture, patient motion, heart sounds, respiration movements, and/or the like. In embodiments, the accelerometer may be used only during recording cycles (e.g., while the sensing/therapy component 312 is sensing physiological parameters such as ECGs, etc.). Accordingly, the controller 304 may be configured to utilize the accelerometer, when it is not being used to detect physiological parameters, to detect impact events.

In embodiments, as shown in FIG. 4, where an IMD 400 includes an accelerometer 402 for detecting physiological parameters, the IMD 400 may include an additional accelerometer 404 for use as an impact event detector, as described throughout this disclosure. FIG. 4 is a schematic block diagram of an IMD 400 illustrating aspects of embodiments of the invention. As shown in FIG. 4, the IMD 400 also includes a power source 406 that powers a controller 408 coupled to a memory 410. The IMD 400 also includes a communications component 412, a sensing/therapy component 414, and a processing unit 416 stored in the memory 410. Although not shown in FIG. 4, the sensing/therapy circuit 414 may be coupled to one or more electrodes and/or other types of sensors. In embodiments, the communications component 412 may be similar to the communications component 210 depicted in FIG. 2 and may include a transceiver and an antenna. In embodiments, any number of the components illustrated in FIG. 4 may be, include, or be similar to, similarly named components depicted in FIG. 2 and/or FIG. 3.

The illustrative IMD 400 shown in FIG. 4 is not intended to suggest any limitation as to the scope of use or functionality of embodiments of the invention disclosed throughout this document. Neither should the illustrative IMD 400 be interpreted as having any dependency or requirement related to any single component or combination of components illustrated therein. For example, in embodiments, the illustrative IMD 400 may include additional components. Additionally, any one or more of the components depicted in FIG. 4 can be, in embodiments, integrated with various ones of the other components depicted therein (and/or components not illustrated). Any number of other components or combinations of components can be integrated with the illustrative IMD 400 depicted in FIG. 4, all of which are considered to be within the ambit of this disclosure.

As described above, in embodiments, a tap sensor (e.g., the tap sensor 216 depicted in FIG. 2, the impact event detector 314 and processing unit 320 combination depicted in FIG. 3, and/or the accelerometer 404 and processing unit 416 combination depicted in FIG. 4) may facilitate transitioning an IMD (e.g., the IMD 102 depicted in FIG. 1, the IMD 202 depicted in FIG. 2, the IMD 300 depicted in FIG. 3, and/or the IMD 400 depicted in FIG. 4) from a first state to a second state in response to an impact event, such as a tap, on an external surface of the patient. In this manner, taps and other external impact events may be used to communicate with an IMD implanted within a patient. FIG. 5 depicts an illustrative method 500 of communicating with an implantable medical device (IMD) in accordance with embodiments of the present invention.

As shown in FIG. 5, the illustrative method includes detecting an impact event (block 502) and generating a detection signal (block 504). In embodiments, an impact event detector (e.g., the impact event detector 222 depicted in FIG. 2, and/or the impact event detector 314 depicted in FIG. 3) may be used to detect the impact event. For example, the impact event detector may be, or include, an accelerometer, an inertial measuring unit (IMU), an acoustic transducer, an electrode, and/or the like. A processing unit (e.g., the processing unit 224 depicted in FIG. 2, and/or the processing unit 320 depicted in FIG. 3) may be used to analyze the detection signal. As shown in FIG. 5, analyzing the detection signal may include determining a characteristic of the detection signal (block 506) and determining that the characteristic of the detection signal satisfies one or more criteria (block 508). In embodiments, for example, the characteristic of the detection signal may relate to a force associated with the impact event, an origination location of the impact event, a number of times that the impact event occurs during a specified time period, a pattern of impact events, a combination of one or more of these characteristics, and/or the like.

In response to determining that the characteristic satisfies the one or more criteria, the IMD may transition from a first state to a second state (block 510). In embodiments, the processing unit may determine that the characteristic of the detection signal does not satisfy the one or more criteria, in which case, the IMD may not transition from a first state to a second state. According to embodiments, the first and second states may correspond to a communications component (e.g., the communications component 212 depicted in FIG. 2, the communications component 310 depicted in FIG. 3, and/or the communications component 412 depicted in FIG. 4), a sensing/therapy component (e.g., the sensing/therapy component 214 depicted in FIG. 2, the sensing/therapy component 312 depicted in FIG. 3, and/or the sensing/therapy component 414 depicted in FIG. 4), and/or the like.

For example, in embodiments, in the first state, the communications component may be dormant and, in the second state, the communications component (or a portion thereof) may be activated so that it begins to listen for an initial communication from a receiving device (e.g., the receiving device 106 depicted in FIG. 1 and/or the receiving device 204 depicted in FIG. 2). In another example, in the first state, a sensing/therapy component may be dormant and, in the second state, the sensing/therapy component may be activated to begin sensing, providing therapy, and/or the like. In embodiments, in a first state, the controller may not be recording sensed physiological parameters, while, in a second state, the controller may be recording sensed physiological parameters. According to embodiments, the first and second states may refer to operating parameters such as, for example, durations of recording cycles (e.g., impact events may be used to select a duration for continuous recording of ECG signals), memory allocations, selections of physiological parameters to sense and/or record, and/or the like.

FIG. 6 depicts an illustrative method for facilitating communication between an implantable medical device and a receiving device in accordance with embodiments of the invention. According to embodiments of the method 600, a sensing/therapy component (e.g., the sensing/therapy component 214 depicted in FIG. 2, the sensing/therapy component 312 depicted in FIG. 3, and/or the sensing/therapy component 414 depicted in FIG. 4) senses physiological parameters (block 602). The sensing/therapy component may include sensing technology and/or therapy technology, and may include any number of sensors, electrodes, transducers, and/or the like. The physiological parameters sensed by the sensing/therapy component may include any number of different types of physiological parameters including, for example, electrocardiograms (ECGs), respiration rates, blood flow rates, blood pressures, temperatures, and/or the like, and may include instantaneous measurements, continuous measurements, waveforms, and/or the like. In embodiments, the illustrative method 600 includes recording the sensed physiological parameters (block 604).

As shown in FIG. 6, a tap sensor (e.g., the tap sensor 216 depicted in FIG. 2, the impact event detector 314 and processing unit 320 combination depicted in FIG. 3, and/or the accelerometer 404 and processing unit 416 combination depicted in FIG. 4) detects an impact event (block 606), which may include an impact of an object with an external surface of the body of the patient. The tap sensor (or a component thereof such as, e.g., a processing unit) determines that the impact event likely comprises a communication directed at the tap sensor (block 608) and causes, in response to determining that the impact event likely comprises a communication directed at the tap sensor, a communication component to listen for an initial communication from a receiving device (block 610). As is further shown in FIG. 6, embodiments of the method 600 include establishing a communication session with the receiving device in response to detecting an initial communication therefrom (block 612), and communicating the recorded physiological parameters to the receiving device (block 614).

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A system, comprising:
an implantable medical device configured to be implanted within a patient's body and to record a physiological parameter measurement, the implantable medical device comprising:
a communication component configured to communicate the physiological parameter measurement to a receiving device; and
a tap sensor comprising:
an impact event detector configured to detect the impact event and generate a detection signal in response thereto, the impact event comprising an impact, by an object, on an external portion of the patient's body; and
a processing unit configured to:
receive the detection signal from the impact event detector;
determine at least one characteristic of the detection signal, wherein the at least one characteristic comprises an amplitude of force with which the object impacted the external portion of the patient's body;
determine whether the amplitude of the force is above a specified threshold, wherein the processing unit is configured to determine that the impact event likely comprises a communication directed at the tap sensor if the amplitude of the force is above the specified threshold; in response to detecting the impact event and determining that the impact event likely comprises a communication directed at the tap sensor, cause the communication component to transition from a first state, in which the communication component is dormant, to a second state, in which the communication component is configured to actively listen for incoming communication; and
modify the threshold using a machine-learning technique; and
a receiving device configured to receive the physiological parameter measurement from the implantable medical device.

2. The system of claim 1, wherein the implantable medical device comprises at least one of an implantable loop recorder (ILR), a cardiac pacemaker, an implantable cardioverter defibrillator (ICD) device, and a cardiac resynchronization therapy (CRT) device.

3. The system of claim 1, wherein the receiving device is an external device.

4. The system of claim 1, the tap sensor comprising at least one of an accelerometer and an inertial measurement unit (IMU).

5. The system of claim 1, wherein the physiological parameter measurement comprises a measurement of a cardiac activation signal.

6. An implantable medical device, configured to be implanted within a body of a patient, the implantable medical device comprising:
a sensing component configured to sense one or more physiological parameters;
a memory configured to store the one or more physiological parameters; and
a tap sensor comprising:
an impact event detector configured to detect an impact event on an external surface of the body of the patient and generate a detection signal in response thereto; and
a processing component configured to:
receive the detection signal from the impact event detector;
determine at least one characteristic of the detection signal, wherein the at least one characteristic of the detection signal comprises an amplitude of force associated with the impact event;
determine whether the amplitude of the force is above a specified threshold, wherein the processing component determines that the impact event likely comprises a communication directed at the tap sensor when the amplitude of the force is above the specified threshold; and
cause, in response to determining that the impact event likely comprises a communication directed at the tap sensor, the implantable medical device to be transitioned from a first state to a second state;
a communication component configured to communicate the one or more physiological parameters to a receiving device, wherein the first state and the second state correspond to the communication component, wherein:
when the implantable medical device is in the first state, the communication component is dormant;
when the implantable medical device transitions to the second state, the communication component begins listening for a communication from the receiving device;
wherein, if the communication component receives an initial communication from the receiving device, the communication component provides an indication of receipt of the initial communication to the processing component; and wherein, if the processing component receives the indication of receipt of the initial communication, the processing component correlates the indication with the specified threshold to facilitate a machine learning technique configured to modify the specified threshold to detect intentional inputs versus accidental inputs.

7. The implantable medical device of claim 6, wherein the implantable medical device comprises at least one of an implantable loop recorder (ILR), a cardiac pacemaker, an implantable cardioverter defibrillator (ICD) device, and a cardiac resynchronization therapy (CRT) device.

8. The implantable medical device of claim 6, wherein the first state and the second state correspond to the sensing component, wherein:
when the implantable medical device is in the first state, the sensing component does not sense the one or more physiological parameters; and
when the implantable medical device is in the second state, the sensing component senses the one or more physiological parameters.

9. The implantable medical device of claim 6, the tap sensor comprising at least one of an accelerometer and an inertial measurement unit (IMU).

10. The implantable medical device of claim 6, wherein the tap sensor is activated and deactivated based on a pulse width modulation (PWM) cycle.

* * * * *